(12) United States Patent
Bentamy et al.

(10) Patent No.: US 10,704,347 B2
(45) Date of Patent: Jul. 7, 2020

(54) METHOD AND APPARATUS FOR ANALYZING GAS FROM DRILLING FLUIDS

(71) Applicant: Geoservices Equipements, Roissy en France (FR)

(72) Inventors: Nassim Bentamy, Roissy-en-France (FR); Paul Bertrand, Roissy-en-France (FR); Mahdi Ammar, Roissy-en-France (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 16/017,009

(22) Filed: Jun. 25, 2018

(65) Prior Publication Data

US 2019/0390524 A1 Dec. 26, 2019

(51) Int. Cl.
| | | |
|---|---|---|
| *E21B 21/06* | (2006.01) | |
| *E21B 21/08* | (2006.01) | |
| *E21B 49/00* | (2006.01) | |
| *E21B 47/14* | (2006.01) | |

(52) U.S. Cl.
CPC ............ *E21B 21/067* (2013.01); *E21B 21/08* (2013.01); *E21B 47/14* (2013.01); *E21B 49/005* (2013.01)

(58) Field of Classification Search
CPC .......... E21B 1/067; E21B 21/08; E21B 47/14; E21B 49/005
See application file for complete search history.

(56) References Cited

U.S. PATENT DOCUMENTS

| | | | |
|---|---|---|---|
| 4,738,528 A | 4/1988 | Craft | |
| 4,836,689 A | 6/1989 | OBrien et al. | |
| 5,145,785 A | 9/1992 | Maggard et al. | |
| 5,453,132 A | 9/1995 | Kowalchuk | |
| 6,474,152 B1* | 11/2002 | Mullins | ............... G01N 21/359 166/250.01 |
| 6,526,805 B1* | 3/2003 | Babes-Dornea | ... G01N 21/3504 73/19.12 |
| 7,741,605 B2 | 6/2010 | Gunn et al. | |
| 7,794,527 B2 | 9/2010 | Sterner | |
| 8,884,215 B2 | 11/2014 | Gunn et al. | |
| 9,707,896 B2 | 7/2017 | Boegel et al. | |
| 2006/0093523 A1* | 5/2006 | Norman | ............. G01N 33/2823 422/83 |
| 2009/0293605 A1* | 12/2009 | Evrard | .................. E21B 49/005 73/152.25 |

(Continued)

FOREIGN PATENT DOCUMENTS

| | | |
|---|---|---|
| EP | 2949520 A1 | 12/2015 |
| EP | 3165710 A1 | 5/2017 |

*Primary Examiner* — Marcus H Taningco

(57) ABSTRACT

A system for analyzing gas extracted from drilling fluid is provided. In one embodiment, the system includes a gas extractor having a gas extraction chamber within a gas extractor housing and a gas outlet for gas separating from the drilling fluid within the gas extraction chamber. Further, the system includes a gas analyzer, which has an optical analyzer and an optical source that are situated outside of the gas extractor. A gas analysis zone is in fluid communication with the gas extraction chamber and is optically connected via at least one fiber optic cable to the optical source and the optical analyzer. Additional methods, systems, and devices are also disclosed.

18 Claims, 8 Drawing Sheets

(56) References Cited

U.S. PATENT DOCUMENTS

| | | | |
|---|---|---|---|
| 2011/0308391 A1* | 12/2011 | DeGreeve | B01D 19/0042 |
| | | | 95/260 |
| 2011/0313670 A1 | 12/2011 | DeGreeve et al. | |
| 2012/0137764 A1* | 6/2012 | Lawrence | E21B 49/005 |
| | | | 73/152.23 |
| 2013/0275047 A1 | 10/2013 | Selman et al. | |
| 2015/0136961 A1 | 5/2015 | Eddy et al. | |
| 2015/0160127 A1 | 6/2015 | DeGreeve et al. | |
| 2016/0273355 A1* | 9/2016 | Gosney | B01D 19/0078 |

* cited by examiner

METHOD AND APPARATUS FOR ANALYZING GAS FROM DRILLING FLUIDS

BACKGROUND

Wells are generally drilled into subsurface rocks to access fluids, such as hydrocarbons, stored in subterranean formations. Drilling fluids (e.g., drilling muds) are used within wells for various reasons, such as to inhibit flow of formation fluids into the wells, to clean and cool drill bits, and to remove wellbore cuttings. Drilling mud can be circulated through a well by pumping the drilling mud from a mud tank at the surface down into a well through a drill string. The drilling mud can exit the drill string at the bottom of the well and then return up the well through the annular space between the drill string and the well walls.

The returning drilling mud may include wellbore cuttings, other debris, and formation fluid. Various equipment can be used to condition and evaluate the returning drilling mud, which may include analyzing formation fluid mixed with the drilling mud to reconstruct the geological succession of formations penetrated during drilling and to assess the types of fluids encountered in the drilled formations. For instance, gaseous formation fluid (e.g., gaseous hydrocarbons, carbon dioxide, and hydrogen sulfide) may be carried up the well by the drilling mud, extracted from the mud at the surface, and analyzed with a gas chromatograph or other device to determine the composition of the gas.

SUMMARY

Certain aspects of some embodiments disclosed herein are set forth below. It should be understood that these aspects are presented merely to provide the reader with a brief summary of certain embodiments and that these aspects are not intended to limit the scope of this disclosure. Indeed, embodiments in accordance with this disclosure may encompass a variety of aspects that may not be set forth below.

In one embodiment of the present disclosure, a system includes a gas extractor and a gas analyzer. The gas extractor has a gas extraction chamber within a gas extractor housing and a gas outlet that allows gas separated from the drilling fluid to exit the gas extraction chamber. The gas analyzer includes an optical analyzer and an optical source that are situated outside of the gas extractor. A gas analysis zone is in fluid communication with the gas extraction chamber and is optically connected via at least one fiber optic cable to the optical source and the optical analyzer.

In another embodiment, an apparatus includes a gas extractor having a gas extraction chamber within a gas extractor housing and a gas outlet that allows gas separated from the drilling fluid to exit the gas extraction chamber. A gas analysis probe is attached at the gas extractor housing to receive and facilitate analysis of the separated gas exiting the gas extraction chamber via the gas outlet.

In a further embodiment, a method includes receiving a drilling fluid in a gas extractor and conveying gas from the drilling fluid to a gas analysis zone. An optical signal is transmitted from an optical source via a fiber optic cable through the gas within the gas analysis zone. The method also includes analyzing the gas, based on the optical signal, with an optical analyzer optically coupled to the gas analysis zone with a fiber optic cable.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION OF SPECIFIC EMBODIMENTS

Specific embodiments of the present disclosure are described below. These described embodiments are examples of the presently disclosed techniques. In an effort to provide a concise description of these embodiments, some features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time-consuming, but would still be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

Certain embodiments of the present disclosure generally relate to the analysis of gas extracted from drilling fluids. More particularly, some embodiments of the present disclosure relate to methods and apparatuses for detecting and measuring gas, such as hydrocarbons C1-C8 (with isomers), i.e. alkanes having from 1 to 8 carbon atoms, from drilling fluids with a gas analysis probe mounted on or within a gas extractor. This may facilitate direct measurement of the gas locally at the gas extractor, rather than routing the gas from the extractor through a gas line to a remote location for analysis. In certain embodiments, the gas analysis probe is provided as a fiber optic probe that is connected to a spectrometer via a fiber optic cable. The fiber optic probe can include a gas cell for receiving the extracted gas, and an optical signal (e.g., infrared radiation) can be routed through the gas within the gas cell and then detected to facilitate characterization of the gas.

Figure 1:
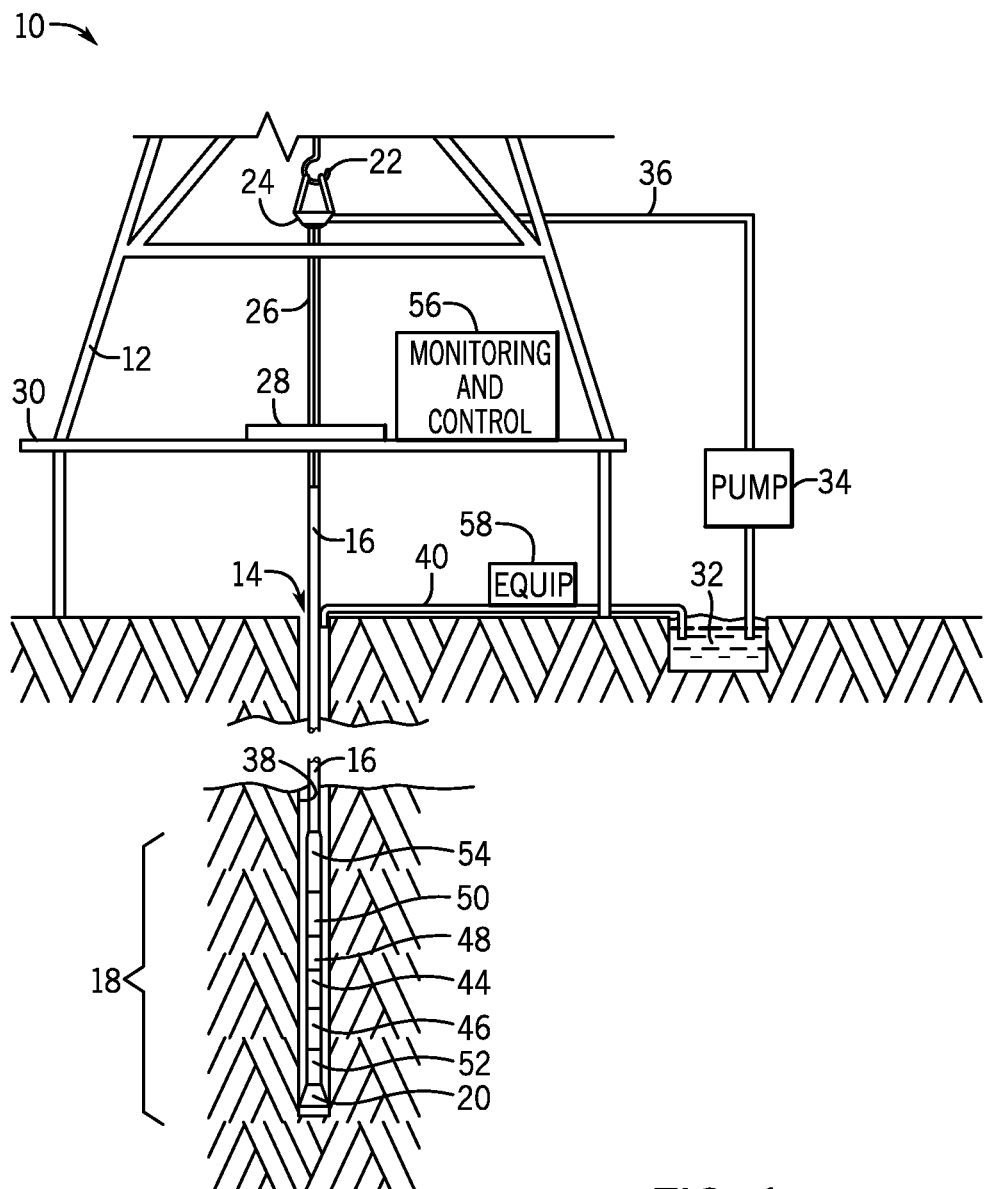
FIG. 1 generally depicts a drilling system with equipment for circulating drilling fluid in accordance with one embodiment of the present disclosure.

Turning now to the drawings, a drilling system 10 at a wellsite is depicted in FIG. 1 in accordance with one embodiment. While certain elements of the drilling system 10 are depicted in this figure and generally discussed below, it will be appreciated that the drilling system 10 may include other components (such as a wellhead assembly) in addition to, or in place of, those presently illustrated and discussed. As depicted, the system 10 includes a drilling rig 12 positioned over a well 14. Although depicted as an onshore drilling system 10, it is noted that the drilling system could instead be an offshore drilling system. The drilling rig 12 supports a drill string 16 that includes a bottomhole assembly 18 having a drill bit 20. The drilling rig 12 can rotate the drill string 16 (and its drill bit 20) to drill the well 14.

The drill string 16 is suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 is coupled to the drill string 16, and the swivel 24 allows the kelly 26 and the drill string 16 to rotate with respect to the hook 22. In the presently illustrated embodiment, a rotary table 28 on a drill floor 30 of the drilling rig 12 is constructed to grip and turn the kelly 26 to drive rotation of the drill string 16 to drill the well 14. In other embodiments, however, a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 is circulated through the well 14 by a pump 34 of a drilling fluid circulation system. The drilling fluid 32 is pumped from a mud pit (or some other reservoir, such as a tank) into the drill string 16 through a supply conduit 36, the swivel 24, and the kelly 26. The drilling fluid 32 exits near the bottom of the drill string 16 (e.g., at the drill bit 20) and returns to the surface through the annulus 38 between the wellbore and the drill string 16. A return conduit 40 (e.g., from a wellhead) transmits the returning drilling fluid 32 away from the well 14. In some embodiments, and as described in greater detail below, the returning drilling fluid 32 is passed through various equipment 58 of the drilling fluid circulation system for conditioning, analysis, and reuse in the well 14.

In addition to the drill bit 20, the bottomhole assembly 18 also includes various instruments that measure information of interest within the well 14. For example, as depicted in FIG. 1, the bottomhole assembly 18 includes a logging-while-drilling (LWD) module 44 and a measurement-while-drilling (MWD) module 46. Both modules include sensors, housed in drill collars, that collect data and enable the creation of measurement logs in real time during a drilling operation. The modules could also include memory devices for storing the measured data. The LWD module 44 includes sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 includes sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules, such as modules 48, 50, 52, and 54 depicted in FIG. 1. Examples of these additional modules include power modules, steering modules, communication modules, and other LWD or MWD modules. It is noted that the bottomhole assembly 18 is modular, and that the positions and presence of particular modules of the assembly could be changed as desired.

The drilling system 10 also includes a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional modules 48, 50, 52, and 54) or surface equipment 58 for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

As noted above, drilling fluid 32 can be circulated through the well 14, and drilling fluid 32 returning from the well 14 may be routed through equipment 58 at the surface. Equipment 58 may include a variety of devices for cleansing or analyzing the returning drilling fluid 32. For instance, the equipment 58 can include solids-control equipment, such as shale shakers, desanders, desilters, or the like for removing wellbore cuttings and other particulates from the returning drilling fluid 32.

Figure 2:
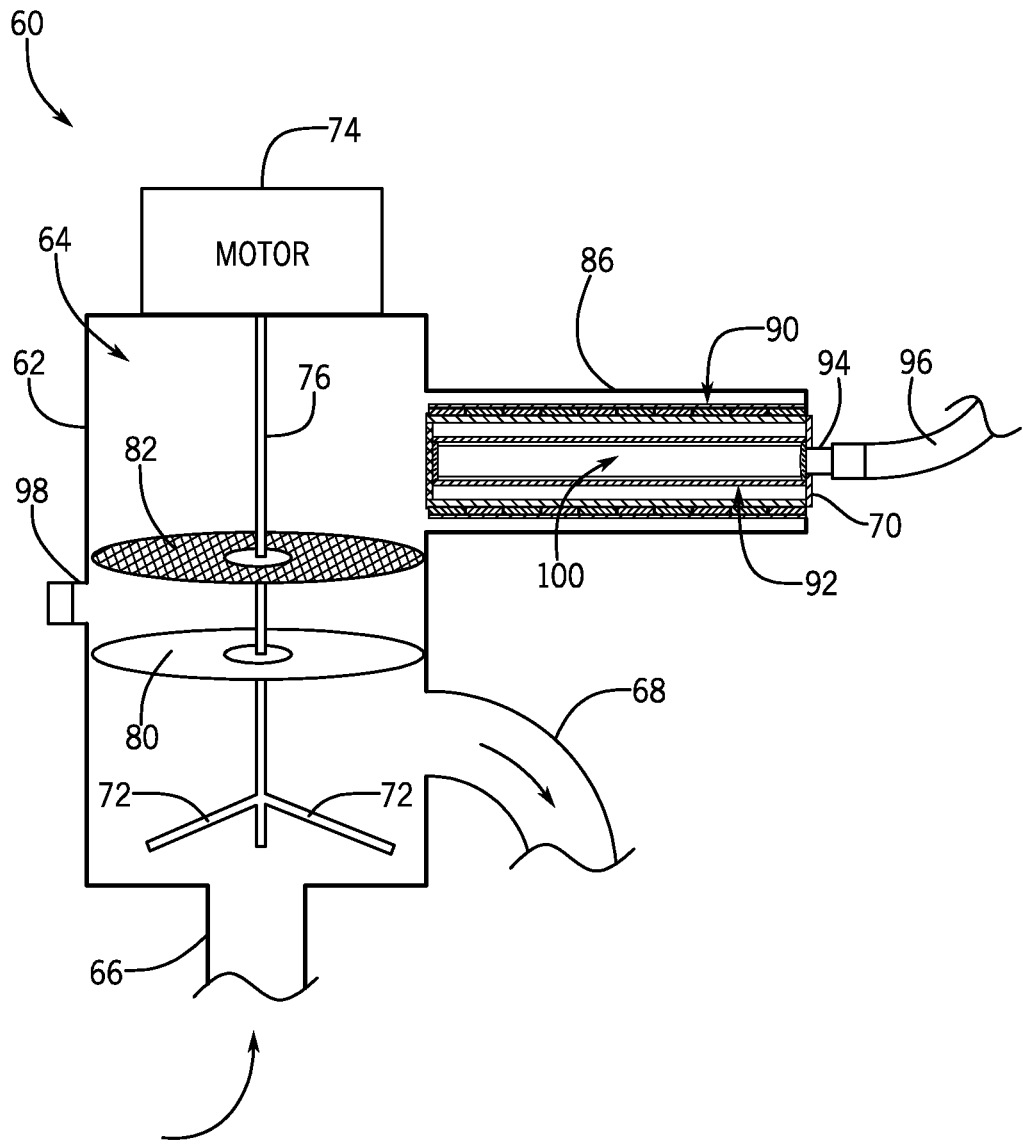
FIG. 2 generally depicts a gas extractor with a gas extraction chamber for separating gas from a drilling fluid and a gas analysis probe used to analyze the gas in accordance with one embodiment.

The equipment 58 can also include a degasser (also referred to as a gas extractor) for removing gas from the returning drilling fluid 32, as well as gas analysis equipment (e.g., a spectrometer or gas chromatograph) for analyzing the gas. An example of a gas extractor 60 used as a component of the equipment 58 is generally illustrated in FIG. 2 in accordance with one embodiment. In this depicted embodiment, the gas extractor 60 includes a housing 62 having a gas extraction chamber 64. The drilling fluid 32 returning from the well 14 can enter the gas extraction chamber 64 through a drilling fluid inlet 66.

As noted above, the drilling fluid 32 returning from the well 14 may include gas, such as gaseous hydrocarbons from a formation penetrated by the well. Gas can be separated from the drilling fluid 32 within the gas extraction chamber 64; separated gas can exit the chamber 64 through a gas outlet 70, while the remaining, degassed drilling fluid 32 can flow out of the chamber 64 through a liquid outlet 68. Although reference is made to degassed drilling fluid and a liquid outlet 68, it will be appreciated that the degassed drilling fluid 32 exiting through the liquid outlet 68 may include some amount of entrained gas that did not separate from the fluid 32 within the gas extraction chamber 64.

In at least some embodiments, including that depicted in FIG. 2, the gas extractor 60 also includes a drilling fluid agitator that facilitates separation of gas from the drilling fluid 32. For example, the gas extractor 60 is shown in FIG. 2 as having an agitator in the form of an impeller with blades 72 rotatable by a motor 74 (such as a pneumatic or electric motor) and a shaft 76 for stirring the drilling fluid 32 and facilitating gas separation within the gas extraction chamber 64. One or more plates, such as discs 80 and 82, can be positioned within the gas extraction chamber 64 to inhibit upward travel of drilling mud or other liquid (such as from splattering) while allowing separated gas to flow past toward the gas outlet 70. As shown in FIG. 2, the disc 80 is a solid plate that allows gas to flow around its outer circumference (i.e., between the disc 80 and the inner wall of the gas extraction chamber 64), while the disc 82 is a grid plate that allows gas to flow through the plate while inhibiting liquids. In other embodiments, however, either or both discs 80 and 82 could be omitted, replaced with another disc, or supplemented with one or more additional discs. The agitator may also have any other appropriate configuration. Still further, in at least some embodiments the gas extractor 60 can be equipped with an automatic positioning system, which may be based on pressure variation detection, fluid level detection (e.g., via ultrasound, radar, proximity switch, paddle, or laser), or mechanical actuation (e.g., a floater), though the position of the gas extractor 60 may instead be static.

The gas extractor 60 depicted in FIG. 2 includes a gas analysis probe 90 positioned within an extension 86 of the housing 62. The architecture of the gas extractor may also be different of what has been shown and the gas analysis probe 90 may be situated elsewhere inside of the gas extractor than in the extension 86. The gas analysis probe 90 is shown as having a gas cell 92 and, accordingly, the gas analysis probe 90 may also be referred to as a gas cell assembly 90. The gas analysis probe 90 also includes a connector 94 (e.g., a subminature assembly (SMA) connector) and a cable 96 that facilitate communication between the probe 90 and other devices, such as gas analyzers.

In at least some embodiments, such as that depicted in FIG. 2, the gas analysis probe 90 is a fiber optic probe that is operatively coupled to a gas analyzer via a fiber optic cable 96. As discussed in greater detail below, the gas analysis probe 90 can be used to analyze, within a gas analysis zone 100, gas extracted from the drilling fluid 32 (e.g., to determine hydrocarbon content). As used herein, "gas analysis zone" means a region for passing a measurement signal (e.g., an optical signal) through a gas to be analyzed. A carrier gas, such as air or helium, can be injected into the gas extraction chamber 64 through a pneumatic connection or inlet 98 to push the separated gas toward the gas analysis probe 90 and the gas outlet 70. Although shown positioned between the discs 80 and 82 in FIG. 2, the pneumatic inlet 98 could be omitted or positioned elsewhere, such as above the disc 82 or below the disc 80.

Figure 3:
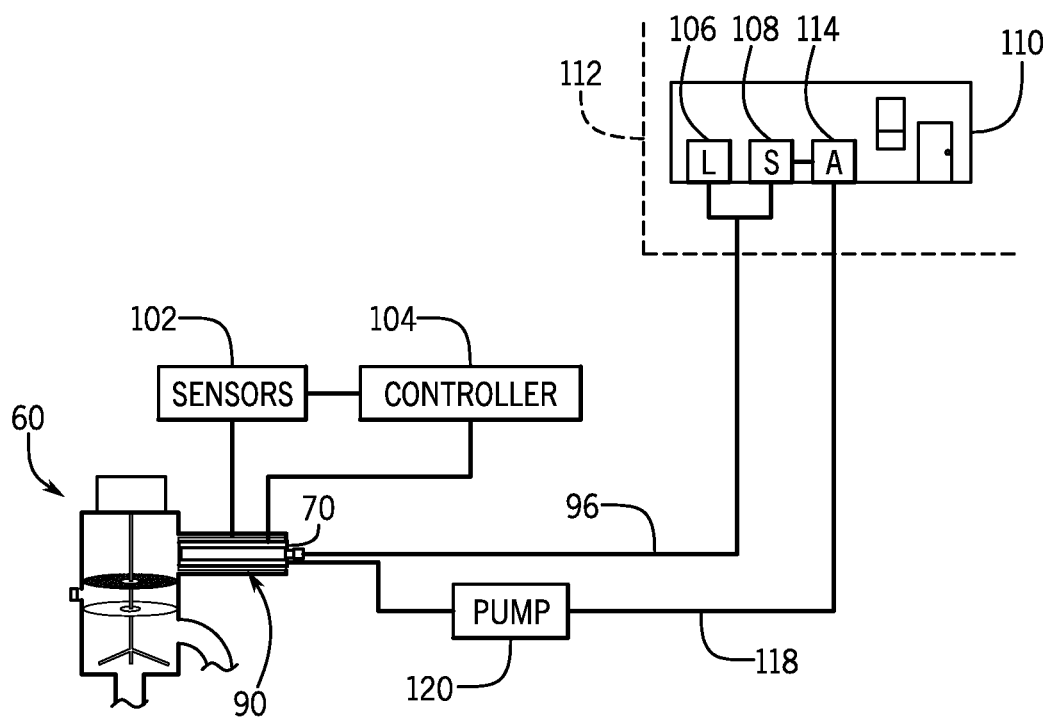
FIG. 3 depicts the gas extractor of FIG. 2 coupled to a remote spectrometer by a cable in accordance with one embodiment.

In addition to the gas analysis probe 90, one or more sensors 102 can be used with the gas extractor 60, as generally depicted in FIG. 3, to measure fluid characteristics or other operating parameters. Each sensor 102 can be installed in series with or parallel to the gas analysis probe 90. The accuracy of measurements acquired with the gas analysis probe 90 may depend on pressure, temperature, and humidity within the gas analysis zone 100. Accordingly, in at least some embodiment the sensors 102 include sensors for measuring some or each of these parameters within the gas analysis zone 100. The measured pressure, temperature, and humidity can be used to refine measurements acquired via the gas analysis probe 90 (e.g., via mathematical error correction) or for quality control. In some instances, the sensors 102 can be used with a controller 104 for regulating one or more operating parameters, such as temperature or pressure. For example, the controller 104 can be a temperature controller that transmits an electrical signal to a resistive heating element of the gas analysis probe 90 in response to input (e.g., temperature or pressure) from one or more sensors 102. Additional sensors 102 can also or instead be used with the gas analysis probe 90.

As will be appreciated, the area (e.g., at a wellsite) in which the gas extractor 60 is installed may be classified as a hazardous area (e.g., an explosive zone). In some embodiments, for instance, the gas extractor 60 is installed along with other equipment in an area classified as a Zone 0, Zone 1 or Zone 2 hazardous area according to International Electrotechnical Commission (IEC) Standard 60079-10-1: 2015 or ATEX Directive 99/92/EC. As used herein, a hazardous area is an area that would be classified as a Zone 0, Zone 1, or Zone 2 hazardous area according to IEC Standard 60079-10-1:2015 or ATEX Directive 99/92/EC, while a non-hazardous area is an area that would not be classified as such a Zone 0, Zone 1, or Zone 2 hazardous area according to IEC Standard 60079-10-1:2015 or ATEX Directive 99/92/EC.

In at least some embodiments, the gas analysis probe 90 is located at the gas extractor 60 to facilitate analysis of the gas separating from the drilling fluid 32 within the gas extraction chamber 64. That is, rather than installing a lengthy gas line from the gas extractor 60 to a remote location (e.g., a mud-logging cabin) and then conveying gas through that gas line to a gas chromatograph or other device for analysis of the gas at the remote location, the gas analysis probe 90 of some embodiments can be used at the gas extractor 60 itself for analysis of the separated gas (e.g., to detect and measure hydrocarbons C1-C5, with isomers, in the gas) without transferring the gas for analysis to a remote location.

A gas analyzer having an optical analyzer and an optical source can be used in some embodiments to analyze gas that has separated from the drilling fluid 32. For instance, the gas analysis probe 90 can be operatively coupled to an optical analyzer, such as a spectrometer 108, by the fiber optic cable 96. As discussed further below, an optical signal can be passed through gas within the gas analysis zone 100 (e.g., within the gas analysis probe 90) and then communicated to the spectrometer 108. The optical signal is modified by interaction with the gas in the gas analysis zone 100. By way of example, a beam of light can be transmitted through the gas within the probe 90 and then conveyed through the fiber optic cable 96 to the spectrometer 108. A light source 106 generating the optical signal may be situated remotely from the probe 90 and conveyed via fiber optic cable 96. The extent of attenuation of the light by the gas within the gas analysis probe 90 depends on the composition of the gas, which allows the spectrometer 108 to analyze the gas via the optical signal received from the gas analysis probe 90 through the fiber optic cable 96. Any suitable light, such as light within the visible, near-infrared, mid-infrared, or far-infrared portions of the electromagnetic spectrum, could be used for gas analysis in accordance with the present techniques. One or more fiber optic cables 96 may be connected to the cell 92 in order to enable simultaneous optical conveyance of the signal coming from the light source 106 and the signal transmitted to the spectrometer 108. The construction of the fiber optic cable 96 may vary between embodiments to accommodate the wavelength of light used. Further, gas analysis via the spectrometer 108 can be performed through various spectroscopic techniques, such as tunable diode laser absorption spectroscopy (TDLAS), Fourier-transform infrared (FTIR) spectroscopy, photoacoustic FTIR spectroscopy, quantum cascade laser (QCL) spectroscopy, or Raman spectroscopy, to name several examples.

The spectrometer 108 can be positioned at any suitable location. In some embodiments, the gas analysis probe 90 is positioned closer to the gas extractor 60 than to the spectrometer 108. More specifically, the gas analysis probe 90 is located within a hazardous area (e.g., at the gas extractor 60) while the spectrometer 108 is in a non-hazardous area in certain embodiments. The dashed line 112 in FIG. 3 generally represents a demarcation between a hazardous area having the gas extractor 60 and a non-hazardous area having the spectrometer 108. The spectrometer 108 can be located within a cabin 110 (e.g., a mud-logging cabin at a wellsite), which may be positioned within a non-hazardous area or may be pressurized such that, when the cabin 110 is used in a hazardous area, the interior of the cabin 110 is itself a non-hazardous area. In some instances, the spectrometer 108 may be positioned 50-100 meters or at an even greater distance from the gas extractor 60. A fiber optic cable is able to convey an optical signal without experiencing losses and therefore is fit for obtaining an accurate measurement with a remote analyzer. This is less challenging than when the gas is conveyed via a gas line to the remote analyzer.

Although the spectrometer 108 may be positioned in a non-hazardous area remote from the gas analysis probe 90, in other embodiments the spectrometer 108 is positioned within a hazardous area along with the gas analysis probe 90. For instance, the spectrometer 108 and the gas analysis probe 90 could be installed in an ATEX Zone 1 or Zone 2 hazardous area. As a further example, in certain embodiments the spectrometer 108 could be installed within five meters of the probe 90, or even within one meter of the probe 90, in an ATEX Zone 1 or Zone 2 hazardous area. The spectrometer 108 could be installed for instance in an explosion-proof box to facilitate deployment within a hazardous area.

Additional analysis equipment 114 may be used (e.g., with the spectrometer 108) for analyzing the gas and deriving one or more properties of the gas in the gas analysis zone 100, such as the quantity of at least one chemical element in the gas or the composition of the gas in the gas analysis zone. In some embodiments, the analysis equipment 114 includes a processor-based analysis unit (e.g., a programmed computer) that derives from an optical analyzer (e.g., the spectrometer 108) one or more properties of the gas in the gas analysis zone as a function of temperature, pressure, or humidity in the gas analysis zone (which may be measured by various sensors 102, as described above). The analysis equipment 114, which could be located in the cabin 110, elsewhere at a wellsite, or at a remote location away from the wellsite, can include a processor-based system or analysis unit that executes stored instructions to compare the intensity of light received by the spectrometer 108 (from the gas analysis probe 90 through the fiber optic cable 96) to the intensity of light emitted into the gas within the gas analysis probe 90, for example. The spectrometer 108 can communicate with the analysis equipment 114 via a wired connection or a wireless connection. In some instances, the analysis equipment 114 includes one or more other gas analyzers, such as a gas chromatograph, that can be used in addition to, or in place of, the spectrometer 108.

In at least one embodiment, the analysis equipment 114 includes a gas chromatograph installed in series with the gas probe assembly 90. As depicted in FIG. 3, for instance, extracted gas can pass through the gas probe assembly 90 and then through a gas line 118 to a gas chromatograph or other gas analyzer of the analysis equipment 114 within the cabin 110. In other embodiments, a gas chromatograph, an additional spectrometer 108, or some other gas analyzer could also or instead be installed in parallel with the gas probe assembly 90 via a different gas outlet of the gas extractor 60. It is noted, however, that while routing the gas through a gas line to a gas chromatograph results in a delayed measurement (resulting from the travel time of the gas from the gas extractor 60 to the gas chromatograph), the optical signal of a fiber optic gas analysis probe 90 travels through the fiber optic cable 96 at a much greater speed that enables substantially instantaneous communication of the signal for analysis by the spectrometer 108, even across large distances.

Although the extracted gas can be pushed out of the gas extractor 60 with a carrier gas injected through the pneumatic inlet 98, in other embodiments the extracted gas can be drawn out of the gas extractor 60 by a downstream pump 120. The pump 120 may take various forms, examples of which include a peristaltic pump, some other positive displacement pump, or a vacuum pump. The pump 120 can be installed in the gas line 118, as depicted in FIG. 3, to draw the extracted gas through the gas outlet 70 of the gas extractor 60 and convey the gas through the gas line 118 to additional equipment for analysis, storage, or disposal. In other instances, the extracted gas is vented to atmosphere (whether pushed by a carrier gas, drawn out via the pump 120, or flowing without assistance) after passing through the gas analysis probe 90.

Figure 4:
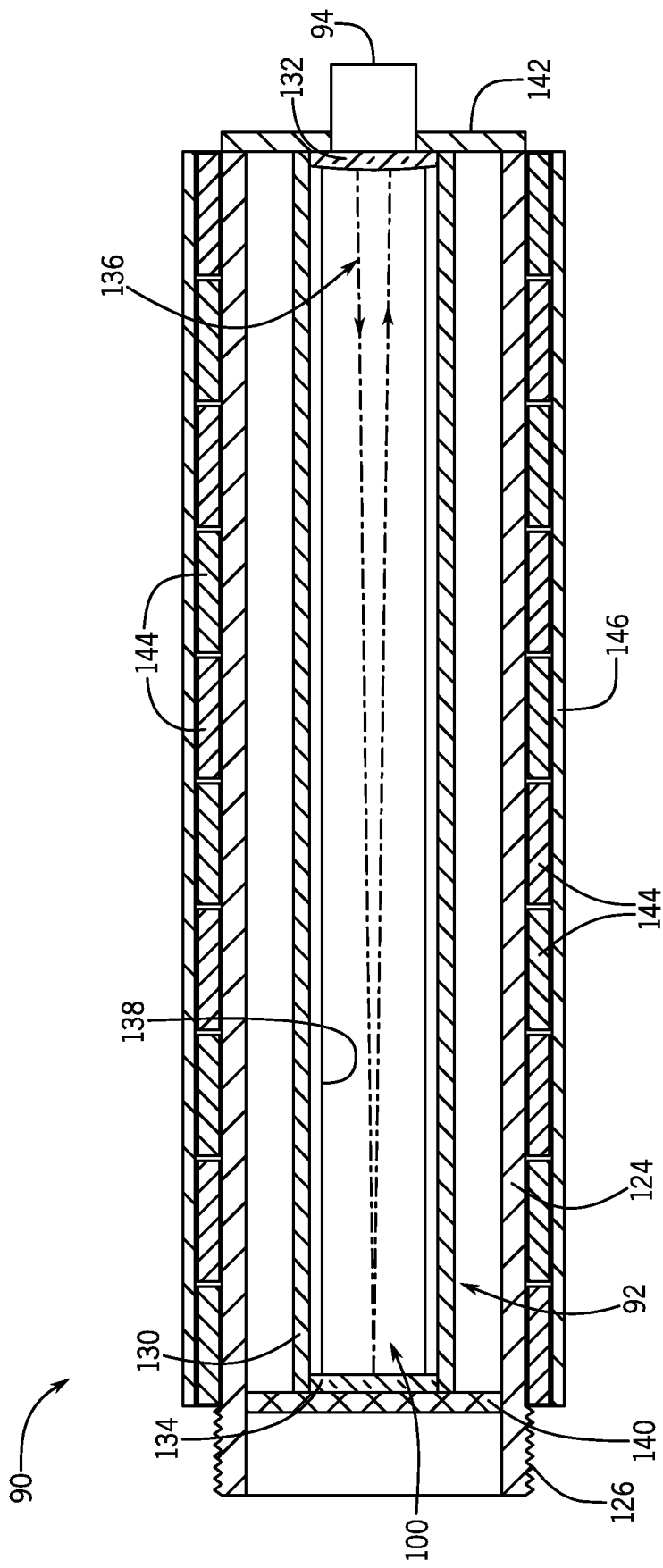
FIG. 4 is a cross-section of a gas analysis probe in accordance with one embodiment.
Figure 5:
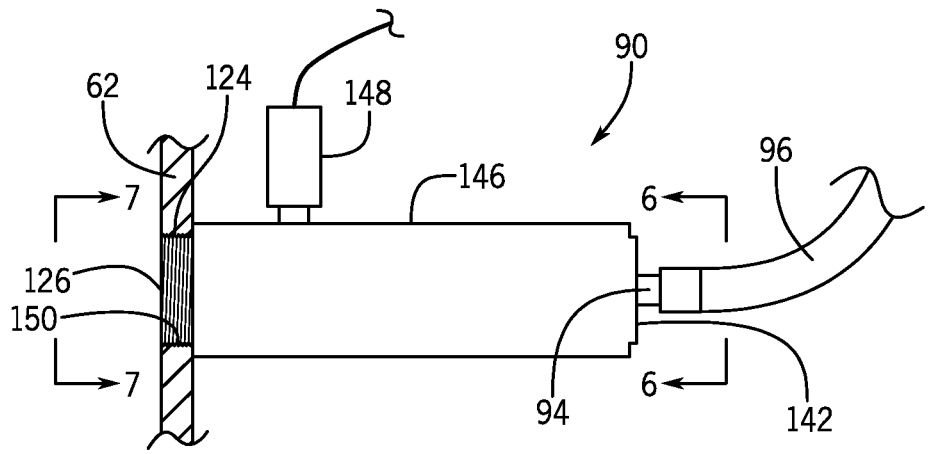
FIG. 5 depicts the gas analysis probe of FIG. 4 threaded into a port of a gas extractor housing in accordance with one embodiment.

In some embodiments, the gas analysis probe 90 is installed inside the gas extractor housing 62, such as within the housing extension 86 as depicted in FIGS. 2 and 3. In some other embodiments, however, the gas analysis probe 90 is instead attached at an exterior of the gas extractor housing 62. By way of example, the gas analysis probe 90 is depicted in FIGS. 4 and 5 in accordance with one embodiment in which the probe 90 includes a threaded end for screwing the probe 90 to the gas extractor housing 62. More specifically, the gas analysis probe 90 of this embodiment differs from that of FIGS. 2 and 3 in than it includes a sleeve 124 having a threaded end 126.

The sleeve 124 houses the gas cell 92, which is depicted as a reflective optical gas cell having a carrier 130 with a lens 132 and a mirror 134. In operation, light 136 can be emitted from a fiber optic connector 94 into gas within the gas cell 92 and then reflected from the mirror 134 toward the connector 94. In at least some embodiments, the gas analysis probe 90 includes an optical fiber for emitting the light 136 into the gas cell 92 and another optical fiber for receiving the light 136 after it has passed through the gas cell 92. The light 136 emitted into the gas cell 92 may be provided from a suitable light source through the fiber optic cable 96 and the light 136 received after passing through the gas cell 92 can be carried as an optical signal by the fiber optic cable 96 to a suitable detector, such as the spectrometer 108. The housing components of the gas analysis probe 90, such as the sleeve 124 and the carrier 130, can be made of stainless steel or any other suitable material (e.g., a material resistant to abrasive and corrosive gas). In one embodiment, if the light source is an infrared light source, the lens 132 is a Zinc Selenide (ZnSe) lens with an anti-reflective coating and the mirror 134 is a copper mirror, but other suitable materials may be used for these components as well. In some embodiments, an optical window may be used instead of a lens.

Gas extracted from drilling fluid 32 within the gas extractor 60 can enter the gas cell 92 in any suitable manner, such as through slots or holes 138 in the body of the carrier 130. One or more filters 140 may be installed in-line with and upstream of the gas cell 92 to remove particles and moisture from the extracted gas prior to analysis. Such filters can include a hydrophobic filter membrane, a demister filter, or a coalescing filter, for example. The gas to be analyzed can flow into the gas cell 92 through the filters 140 and then exit through an end 142 of the gas analysis probe 90.

The gas cell 92 can be used, continually or continuously in some cases, for analyzing gas exiting the gas extractor 60. Although an optical path of the light 136 is depicted in FIG. 4 as an example, it will be appreciated that the optical path of the light 136 will differ in other embodiments. For instance, the length of the gas cell 92 may vary between embodiments or the light 136 may be reflected multiple times within the gas cell 92 to increase its path length. In other embodiments, the gas cell 92 may be a non-reflective optical gas cell that omits the mirror 134, with the light 136 emitted from an optical fiber at one end of the gas cell 92 and received by another optical fiber at the opposite end. In such cases, a pair of SMA or other connectors 94 could be spaced apart and used to couple the emitting and receiving optical fibers.

As generally noted above, the gas measurement obtained with the gas analysis probe 90 can be influenced by temperature. A measurement apparatus using the gas analysis probe 90 with an infrared spectrometer 108, for instance, may be calibrated for a given temperature, such as 50° C. Accordingly, some embodiments include temperature regulation to facilitate measurement. By way of example, the gas analysis probe 90 is depicted in FIG. 4 as having heating tape 144 wrapped around the exterior of the sleeve 124. A temperature sensor 102 can be used to measure temperature within the gas analysis probe 90, and during analysis of the gas the controller 104 can regulate the temperature inside the gas analysis probe 90 via the heating tape 144 in response to the measured temperature. A cover 146 could also be positioned about the heating tape 144, such as shown in FIG. 4.

In some embodiments, the gas analysis probe 90 is mounted to the gas extractor housing 62. Although the gas analysis probe 90 can be mounted to the gas extractor housing 62 in various manners, in some embodiments the gas analysis probe 90 includes a threaded end (e.g., the threaded end 126) screwed into a port of the gas extractor housing 62. An example of this is shown in FIG. 5 in accordance with one embodiment. More specifically, FIG. 5 depicts the gas analysis probe 90 of FIG. 4 threaded into a port 150 of the gas extractor housing 62 with mating threads. In this manner, the gas analysis probe 90 can be mounted to the exterior of the housing 62 to receive gas separated from the drilling fluid 32 for analysis. As noted above, additional sensors 102 can be connected to the gas analysis probe 90; one example of this is shown in FIG. 5 as a sensor 148 (e.g., a pressure sensor) connected to the probe 90.

Figure 6:
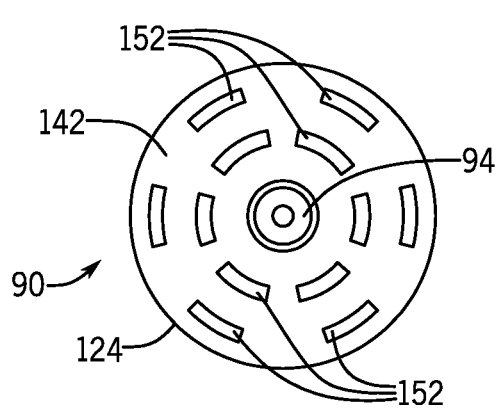
FIGS. 6 and 7 are elevational views of opposing ends of the gas analysis probe of FIGS. 4 and 5 in accordance with one embodiment.
Figure 7:
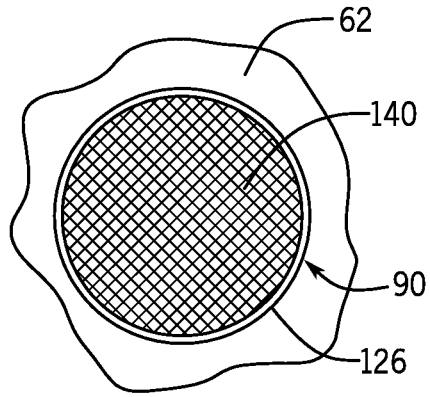

The end 142 of the gas analysis probe 90 can have one or more outlets to allow gas to exit the probe 90. The configuration of these outlets can vary between embodiments, but FIG. 6 depicts the end 142 as having outlet slots 152 that allow gas to exit from the probe 90 after passing the gas cell 92. FIG. 7 is an elevational view of the opposite end of the gas analysis probe (from inside the gas extractor housing 62) and depicts the filter 140 through which gas may flow from the gas extraction chamber 64 to the gas cell 92.

Figure 8:
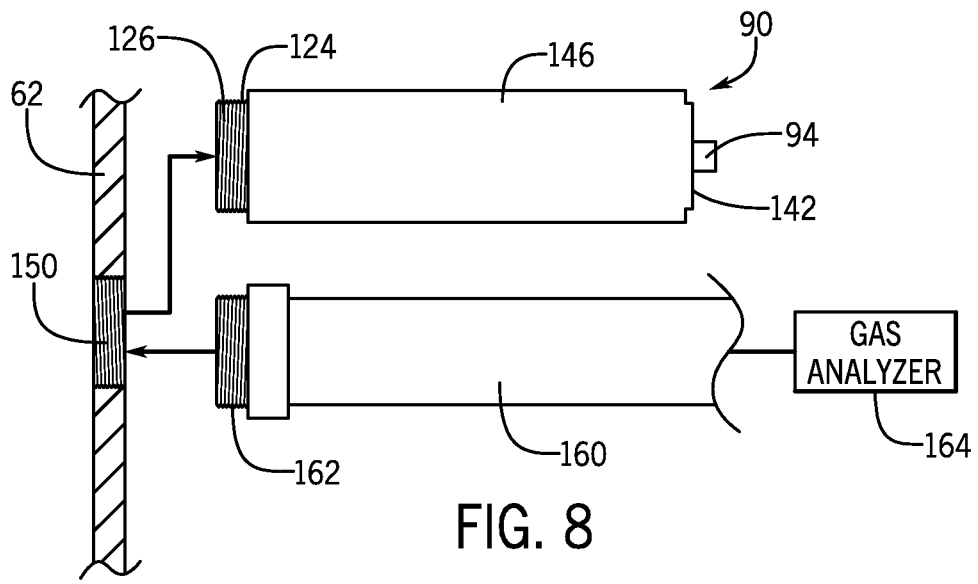
FIG. 8 generally depicts removing the gas analysis probe of FIGS. 4 and 5 from the gas extractor housing and connecting a gas line in place of the gas analysis probe for use with a different gas analyzer in accordance with one embodiment.

The gas extractor 60 may be designed for interchangeable use with different types of gas analyzers. As depicted in FIG. 8, for instance, the gas analysis probe 90 can be unscrewed from the threaded port 150, and a gas line 160 (e.g., a pipe or hose) can be connected via a fitting 162 threaded into the port 150 in place of the gas analysis probe 90. The gas line 160 can route the separated gas from the gas extractor 60 to another gas analyzer 164, such as a gas chromatograph. Moreover, this convertibility can provide operational flexibility and facilitate use of the gas extractor 60 in a wider variety of applications. In some cases, for example, the gas extractor 60 could be used with a spectrometer 108 connected in communication with a gas analysis probe 90 installed at the gas extractor 60 (e.g., installed in the port 150), while in others a gas chromatograph can be connected to receive gas from the gas extractor 60 through a gas line 160 fastened to the port 150. That is, the gas analysis probe 90 can be disconnected from the gas extractor 60, and a gas chromatograph can be coupled to the gas extractor 60 with the gas line 160 in place of the disconnected gas analysis probe 90.

Figure 9:
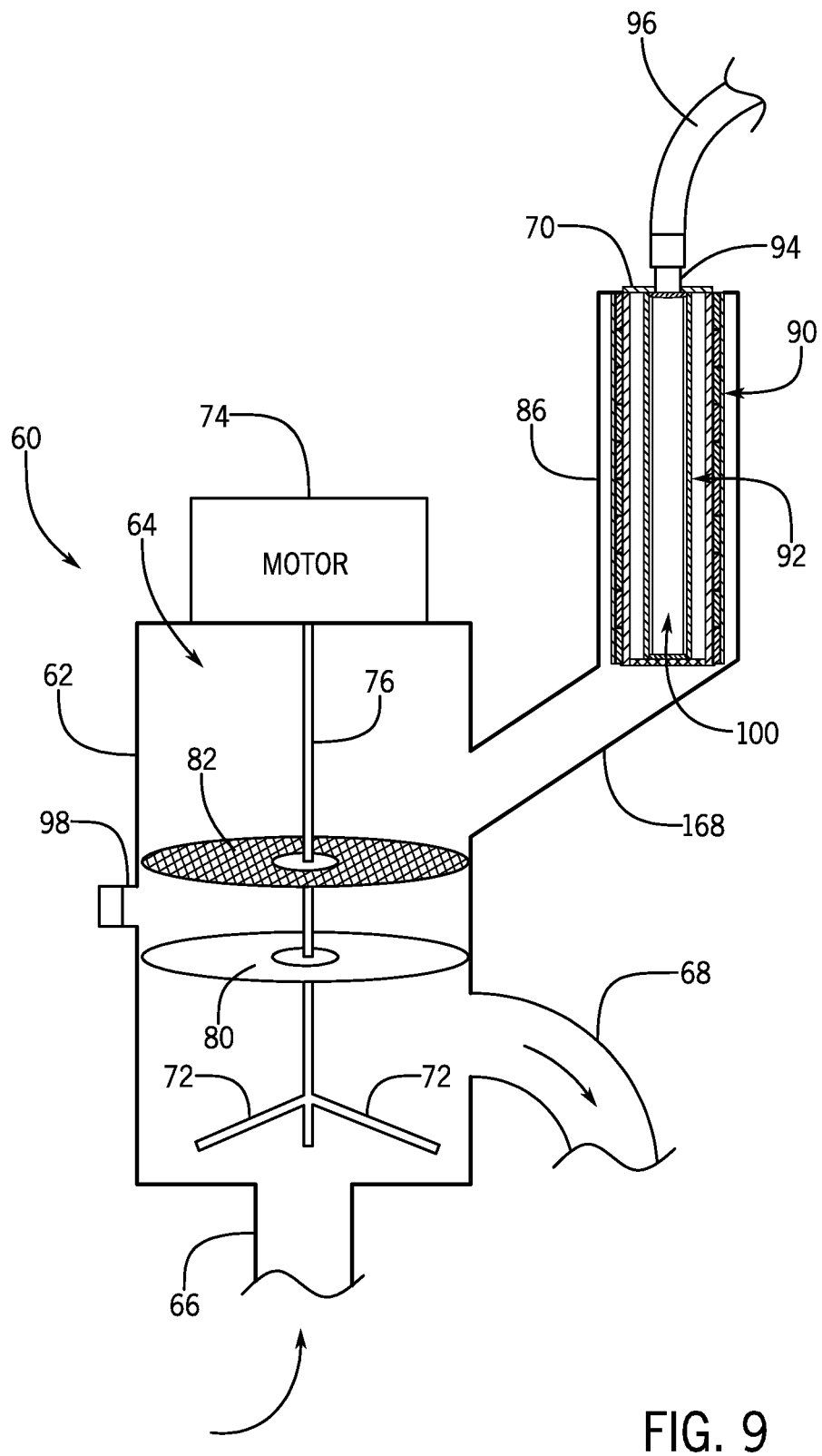
FIG. 9 depicts a gas extractor like that of FIG. 2, but in which the gas analysis probe is installed in a vertical orientation, rather than a horizontal orientation, in accordance with one embodiment.

Although the gas analysis probe 90 may be arranged horizontally, such as shown in FIGS. 2, 3, and 5, in other embodiments the gas analysis probe 90 may be provided in some other orientation. In FIG. 9, for instance, the gas analysis probe 90 is arranged vertically and is offset from the gas extraction chamber 64 by a tube or other conduit 168 to reduce the travel of particles and moisture to the probe 90. Regardless of its orientation, the distance of the gas analysis probe 90 from the gas extraction chamber 64 may vary between different embodiments. And while the gas analysis probe 90 is installed directly at the gas extractor 60 in some embodiments, a gas line could convey gas to a gas analysis probe 90 positioned apart from the gas extractor 60 in other embodiments. Still further, certain embodiments can include multiple gas analysis probes 90 installed in parallel and connected to different gas analyzers for analyzing gas from the gas extractor 60.

Figure 10:
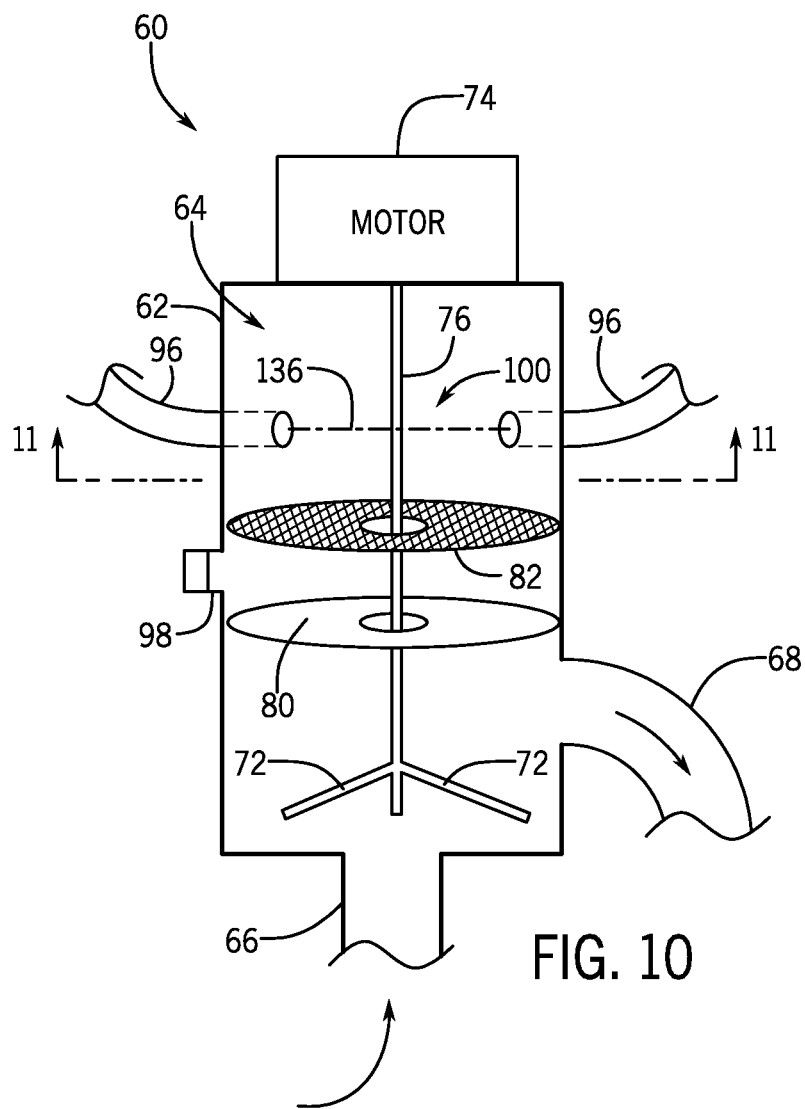
FIGS. 10 and 11 depict a gas extractor arranged to facilitate gas analysis without a gas analysis probe in accordance with one embodiment.
Figure 11:
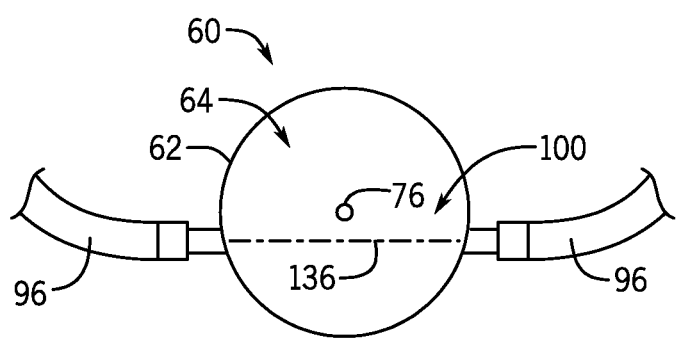

Moreover, in some embodiments the gas extracted from the drilling fluid 32 can be analyzed without a probe or gas cell. In an embodiment generally depicted in FIGS. 10 and 11, for example, gas separated from the drilling fluid 32 within the gas extraction chamber 64 can be analyzed with an optical signal (e.g., light 136) emitted through a gas analysis zone 100 within the gas extraction chamber 64 itself. As depicted, fiber optic cables 96 can be used to transmit the optical signal to and from the gas extractor 60 (e.g., to the gas extractor 60 from the light source 106 and from the gas extractor 60 to the spectrometer 108). In such an embodiment, the gas analysis zone 100 includes at least a portion of the gas extraction chamber 64. In other instances, however, the gas analysis zone 100 may be in fluid communication with the gas extraction chamber 64 but provided elsewhere within the gas extractor 60, such as within the extension 86 (with or without a gas analysis probe 90). In still further embodiments, the gas analysis zone 100 may be positioned outside of the gas extractor 60 and, in at least some of these embodiments, the gas analysis zone 100 may be positioned closer to the gas extractor 62 than to an optical analyzer for analyzing an optical signal that has passed through the gas analysis zone 100.

Finally, it will be appreciated that gas extracted from drilling fluid may not be clean. That is, the extracted gas may include solid particles, humidity, oil, corrosive components, contaminants, and the like, which may wear or foul optical elements of a gas cell. Gas cells can be disassembled to remove condensation and clean the optical elements. In some embodiments of the present technique, however, the gas cell 92 is a self-cleaning gas cell.

Figure 12:
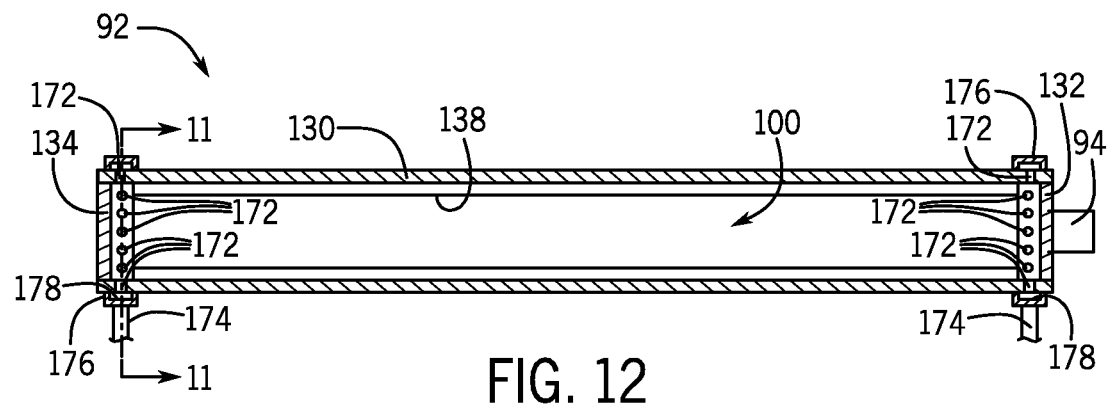
FIG. 12 depicts a self-cleaning gas cell with ports for injecting a cleaning fluid in accordance with one embodiment.
Figure 13:
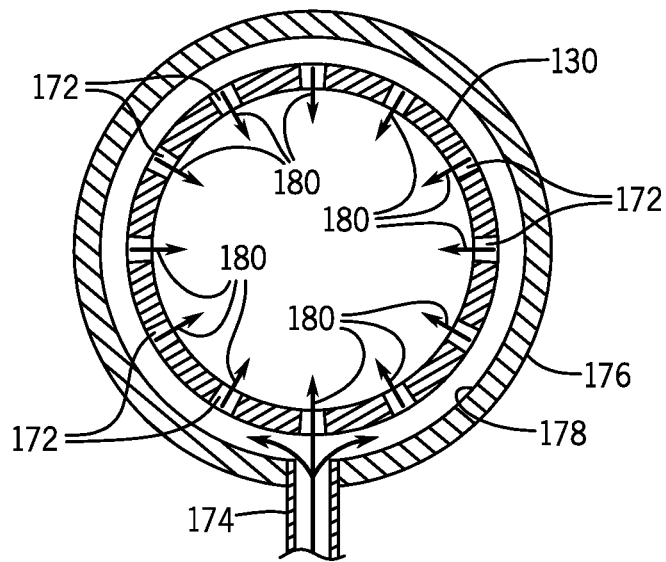
FIG. 13 is a cross-section of the gas cell of FIG. 12 and shows routing of the cleaning fluid into the interior of the gas cell through the ports in accordance with one embodiment.

One example of such a gas cell 92 is generally provided in FIGS. 12 and 13. In this depicted embodiment, the gas cell 92 includes cleaning nozzles or ports 172 near the lens 132 and the mirror 134. A fluid, such as pressurized air, can be injected inside the gas cell 92 through the ports 172 to clean the lens 132 and the mirror 134. In some instances, one or more bursts of air or another cleaning fluid may be provided via the ports 172 to flush dust, condensation, or other fouling agents from the optical surfaces. The cleaning fluid could also or instead be injected continuously through the ports 172 onto or across gas-facing surfaces of the lens 132 and of the mirror 134 to reduce or avoid direct contact of dirty gas with the optical surfaces. The analysis system can be calibrated to properly account for dilution of the gas to be analyzed with the cleaning fluid injected into the gas cell 92. Whether provided continuously or in flushing bursts, the air or other cleaning fluid can be provided at a controlled rate. The rate at which the cleaning fluid is continuously provided to inhibit fouling of the optical surfaces may be less than the rate for flushing fouling agents from the optical surfaces. And in at least one embodiment, the flow rate is controlled using a sonic nozzle.

In FIGS. 12 and 13, supply hoses 174 provide the cleaning fluid to distribution rings 176 that include channels 178 for routing the cleaning fluid to the ports 172 such that the cleaning fluid jets into the gas cell 92 interior (as generally represented by arrows 180) for cleaning the optical surfaces. But the air or other cleaning fluid can be provided to the gas cell 92 in any other suitable fashion. Still further, these self-cleaning techniques could be used to clean optical elements of other gas cells, such as lenses, mirrors, and optical windows, as well as gas cell filtering systems (e.g., filter 140).

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A system for analyzing fluid returning from a well at a surface of a subterranean formation comprising:
   a gas extractor disposed at the surface including:
      a gas extraction chamber within a gas extractor housing; and
      a gas outlet in fluid communication with the gas extraction chamber so as to allow gas separated from a drilling fluid within the gas extraction chamber to exit the gas extraction chamber; and wherein the gas extractor includes:
      a drilling fluid inlet in fluid communication with the gas extraction chamber so as to allow the drilling fluid returning from the well to enter the gas extraction chamber;
      a liquid outlet in fluid communication with the gas extraction chamber so as to allow liquid of the drilling fluid within the gas extraction chamber to exit the gas extraction chamber,
      a gas agitator to facilitate separation of gas from the drilling fluid in the gas extraction chamber,
   a gas analyzer including an optical analyzer and an optical source that are situated outside of the gas extractor, wherein a gas analysis zone in fluid communication with the gas extraction chamber is optically connected via at least one fiber optic cable to the optical source and the optical analyzer, wherein the gas extractor includes the gas analysis zone.

2. The system of claim 1, wherein the gas analysis zone is positioned closer to the gas extractor than to the optical analyzer.

3. The system of claim 1, wherein the gas analysis zone includes at least a portion of the gas extraction chamber.

4. The system of claim 1, wherein the system is configured so that the optical source transmits an optical signal via the at least one fiber optic cable to the gas analysis zone and that the optical signal modified by interaction with the separated gas in the gas analysis zone is conveyed to the optical analyzer.

5. The system of claim 4, comprising a mirror to reflect the optical signal transmitted by the optical source in the gas analysis zone.

6. The system of claim 1, comprising an analysis unit to derive from the optical analyzer one or more properties of the gas in the gas analysis zone.

7. The system of claim 6, wherein the one or more properties includes a quantity of at least one chemical element in the gas or a composition of the gas in the gas analysis zone.

8. The system of claim 1, wherein the optical analyzer comprises one or more of the following: a tunable diode laser absorption spectrometer (TDLAS), a Fourier-transform infrared (FTIR) spectrometer, a quantum cascade laser (QCL) spectrometer, or a Raman spectrometer.

9. The system of claim 1, comprising at least one of a temperature sensor, a pressure sensor, or a humidity sensor in the gas analysis zone.

10. The system of claim 9, comprising an analysis unit to derive from the optical analyzer one or more properties of the gas in the gas analysis zone as a function of measurements obtained by the at least one of the temperature sensor, the pressure sensor, or the humidity sensor in the gas analysis zone.

11. The system of claim 1, comprising a temperature regulation unit in order to regulate the temperature in the gas analysis zone.

12. The system of claim 1, wherein the gas extractor is installed at a wellsite to receive the drilling fluid extracted from a wellbore.

13. The system of claim 1, wherein the gas analysis zone is positioned within a hazardous area and the optical analyzer is positioned in a non-hazardous area.

14. A system for analyzing fluid returning from a well at a surface of a subterranean formation comprising:
 a gas extractor disposed at the surface including:
  a gas extraction chamber within a gas extractor housing; and
  a gas outlet in fluid communication with the gas extraction chamber so as to allow gas separated from a drilling fluid within the gas extraction chamber to exit the gas extraction chamber; and
 a gas analyzer including an optical analyzer and an optical source that are situated outside of the gas extractor, wherein a gas analysis zone in fluid communication with the gas extraction chamber is optically connected via at least one fiber optic cable to the optical source and the optical analyzer, comprising a gas analysis cell mounted to the gas extractor housing so that the gas analysis cell contacts the gas extractor housing, wherein he gas analysis cell is configured to receive and facilitate analysis of the separated gas exiting the gas extraction chamber via the gas outlet.

15. The system of claim 14, comprising one or more filters positioned to filter the separated gas entering the gas analysis zone.

16. The system of claim 14, wherein the gas analysis cell includes a self-cleaning gas cell configured to clean at least one element of the gas cell.

17. A method for analyzing fluid returning from a well at a surface of a subterranean formation comprising:
 receiving a drilling fluid returning from the well in a gas extractor disposed at the surface, wherein the gas extractor includes a gas extractor housing, and a gas extraction chamber;
 agitating the drilling fluid in the gas extraction chamber with an agitator to extract a gas from the drilling fluid;
 conveying the extracted gas to a gas analysis zone in the gas extractor chamber;
 transmitting an optical signal from an optical source via a fiber optic cable and through the gas within the gas analysis zone; and
 analyzing the gas, via the optical signal, with an optical analyzer optically coupled to the gas analysis zone via the fiber optic cable or an additional fiber optic cable.

18. The method of claim 17, comprising:
 disconnecting a fiber optic gas cell assembly from the gas extractor; and
 connecting a gas chromatograph to the gas extractor via a gas line connected to the gas extractor in place of the disconnected fiber optic gas cell assembly.

* * * * *